United States Patent [19]
Arthaud et al.

[11] Patent Number: 5,932,796
[45] Date of Patent: Aug. 3, 1999

[54] APPARATUS FOR THE DETERMINATION OF THE FLASHPOINT OF A SUBSTANCE

[75] Inventors: Didier Arthaud, Limonest; Alain Piquemal, St Didier sous Riviere; Frédéric Tort, Saint Genis Laval, all of France

[73] Assignee: Elf Antar France, Courbevoie, France

[21] Appl. No.: 08/942,030

[22] Filed: Oct. 1, 1997

[30] Foreign Application Priority Data

Oct. 3, 1996 [FR] France .................................. 96 12081

[51] Int. Cl.$^6$ .................................................. G01N 25/52

[52] U.S. Cl. .................................................. 73/36; 374/8

[58] Field of Search ................ 73/36; 374/8; 250/554; 340/578

[56] References Cited

U.S. PATENT DOCUMENTS

| | | | |
|---|---|---|---|
| 3,011,337 | 12/1961 | McGlynn | 73/36 |
| 3,692,415 | 9/1972 | Shiller | 250/554 |
| 4,701,624 | 10/1987 | Kern et al. | 250/554 |
| 5,176,449 | 1/1993 | Grabner | 73/36 |
| 5,869,343 | 2/1999 | Handschuck et al. | 73/36 |

*Primary Examiner*—John E. Chapman
*Attorney, Agent, or Firm*—Oblon, Spivak, McClelland, Maier & Neustadt, P.C.

[57] ABSTRACT

An apparatus for determining the flashpoint of a substance, including a test cup adapted to contain the substance, a heating element which heats the substance, a tube and a needle valve which produce a calibrated flame, a temperature sensor which measures the temperature of the substance, and an optical detector, having at least one optical fiber, which detects variations in the light intensity from the flame, or from the ignited vapor emitted by the substance.

9 Claims, 5 Drawing Sheets

FIG. 1
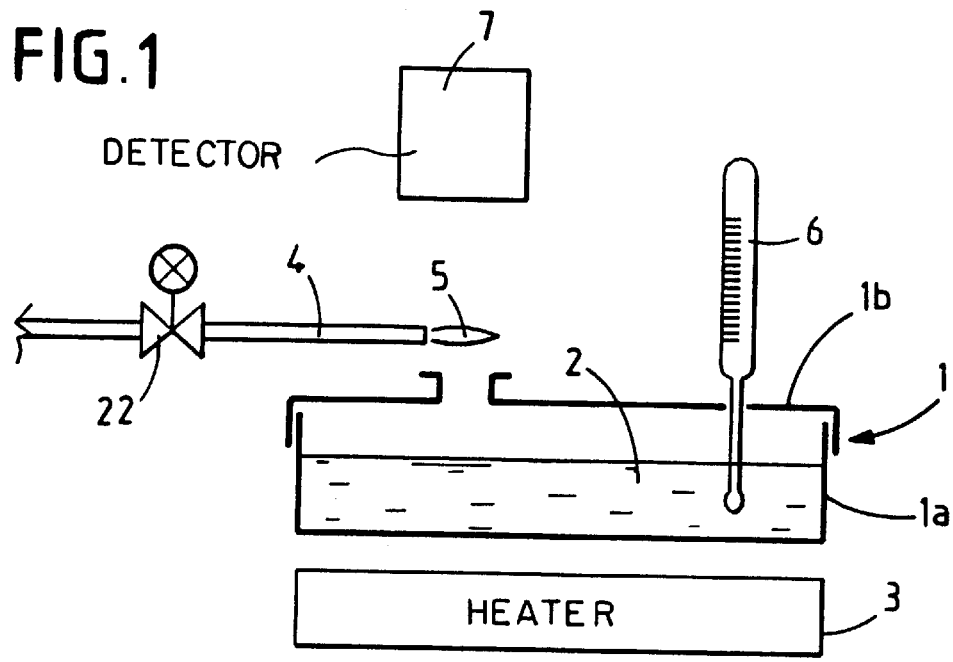
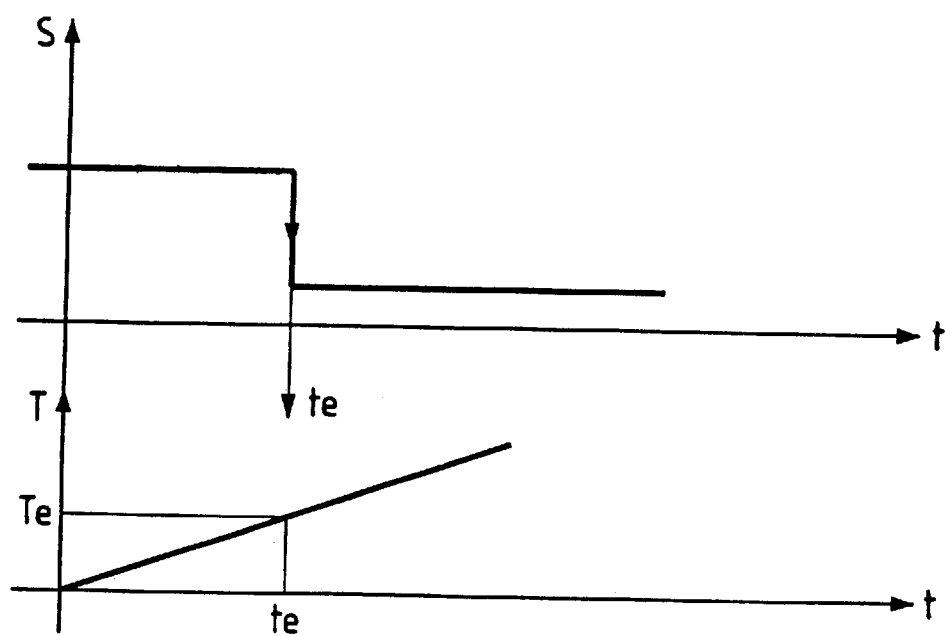
FIG. 3

APPARATUS FOR THE DETERMINATION OF THE FLASHPOINT OF A SUBSTANCE

TECHNICAL FIELD

The present invention relates to an apparatus for the determination of the flashpoint of a liquid or solid substance.

It is applicable in research laboratories, testing laboratories and safety departments in industries in which flammable substances are manufactured and/or used.

STATE OF THE PRIOR ART

The flashpoint of a liquid is the minimum temperature to which it must be raised in order for the vapor emitted to ignite spontaneously in the presence of a flame, under standardized conditions.

A method of determining the flashpoint of a liquid substance in a closed cup is described in Standard NF T 60–103, December 1968.

According to this first method, the substance is introduced into a cup consisting of a crucible closed at its upper part by a lid provided with a small opening extended to the outside of the crucible by a small chimney. The substance is heated gradually and without any interruption at a rate of from 2 to 3 degrees Celsius per minute. A small flame of approximately 4 mm in length is maintained just above the chimney of the lid. The flashpoint is the temperature of the substance at which a flash occurs at the exit of the chimney of the lid. The equipment for implementing this method is described in detail in Standard NF T 60–103 and essentially comprises two crucibles and their lid, an ignition device, a heating device, a thermometer and a crucible support.

A method of determining the flashpoint of a liquid substance in an open cup is described in Standard ISO 2592: 1973. The corresponding European standard bears the reference EN 22592: 1993.

According to this second method, the substance is introduced into a cup to a specified level. The substance is firstly heated rapidly and then at a uniform and slow rate when approaching the flashpoint temperature. At specified temperature intervals, a small test flame is passed above the surface of the substance. The lowest temperature at which application of the flame causes the vapor emitted by the surface of the substance to ignite is regarded as the flashpoint. The equipment for implementing this method constitutes the open-cup Cleveland apparatus, the description of which is given in the appendix of Standard ISO 2592; it is composed of a test cup, a heating plate, a device enabling the test flame to be presented, a heating device, and supports.

The use of the apparatuses for implementing these methods is manual and the detection of the ignition of the vapor produced is visual.

These apparatuses have been improved by adding a vapor-ignition detector of the ionization type, a substance-temperature sensor and an electronic means for processing the signals emitted by the ignition detector and the temperature sensor. Such a known detector consists of two metal electrodes placed above the surface of the substance in the region of ignition of the vapor emitted by the heated substance.

When the ignition phenomenon occurs, the interelectrode space becomes conducting, the electronic processing means detects this conduction and records the value of the substance temperature.

These apparatuses have the drawback of being disturbed by the foam which forms at the surface of the substance, especially when the latter contains water and when it is heated to a high temperature.

In addition, since the electrodes are placed in the vapor ignition region, they rapidly become soiled by deposition of the products of combustion of this vapor and by this vapor itself, thereby requiring them to be cleaned frequently.

SUMMARY OF THE INVENTION

The object of the invention is specifically to remedy these drawbacks and in particular to provide an apparatus for the determination of the flashpoint of a substance, which is insensitive to the foam forming at the surface of the substance, is not very sensitive to fouling and is easy to clean.

It is applicable in test laboratories and research laboratories in the petroleum industries and more generally in industries which manufacture or use flammable substances.

To this end, the invention proposes an apparatus for the determination of the flashpoint of a substance, comprising a test cup intended to contain the substance, means for heating the substance, means for producing a calibrated flame, and an element for measuring the temperature of the substance, characterized in that it includes, in addition, optical means for detecting variations in light intensity.

According to another characteristic of the invention, the test cup being of the closed type provided with a lid having an opening for presentation of the flame, the optical means for detecting variations in light intensity comprise at least one optical fiber having a first end and a second end, the first end being placed outside the test cup so as to sense part of the light radiation emitted by the flame, the said part of the light radiation propagating inside the optical fiber as far as the second end.

According to another characteristic, the apparatus of the invention includes:

- a converter which converts light into an electrical signal, having an optical input to which the second end of the optical fiber is connected and an electrical analogue output;
- a module for detecting the disappearance of the flame, provided with an analogue input linked to the analogue output of the light converter and with a logic output which delivers an electrical signal indicative of the disappearance of the flame; and
- an electronic device connected to the logic output of the module for detecting the disappearance of the flame and to the element for measuring the temperature, the said device recording the value of the temperature of the substance at the moment when the electrical signal indicative of the disappearance of the flame appears.

According to another characteristic of the invention, the test cup, the means for producing a calibrated flame and the first end of the optical fiber are placed inside an opaque enclosure which protects them from the ambient light.

According to another characteristic, the apparatus of the invention includes an indicator of the size of the flame, provided with an input connected to the electrical analogue output of the light converter.

According to another characteristic of the invention, the test cup being of the open type and the substance emitting vapor, the optical means for detecting variations in light intensity include a converging lens placed above the surface of the substance, at least one optical fiber having a first end and a second end, the first end being placed at the optical focus of the converging lens so as to sense part of the light radiation emitted by the vapor of the substance, said vapor being ignited by the flame, the said part of the light radiation propagating inside the optical fiber as far as the second end.

According to another characteristic of the invention, the test cup being of the closed type provided with a lid having a first opening for presentation of the flame and the vapor-emitting substance, the optical means for detecting variations in light intensity include at least one optical fiber having a first end and a second end, the first end, which passes through a second opening made in the lid, is placed inside the test cup so as to sense part of the light radiation emitted by the vapor of the substance, said vapor being ignited by the flame, the said part of the light radiation propagating inside the optical fiber as far as the second end.

According to another characteristic, the apparatus of the invention includes:

a converter which converts light into an electrical signal, having an optical input to which the second end of the optical fiber is connected, and an electrical analogue output;

a light-flash detection module provided with an analogue input linked to the analogue output of the light converter and with a logic output which delivers an electrical signal indicative of the ignition of the vapor of the substance; and an electronic device connected to the logic output of the light-flash detection module and to the element for measuring the temperature, the said device recording the value of the temperature of the substance at the moment when the vapor of the substance is ignited by the flame.

BRIEF DESCRIPTION OF THE DRAWINGS

The invention will be more clearly understood on reading the detailed description of various embodiments with reference to the appended drawings in which:

FIG. 1 shows diagrammatically an apparatus for the determination of the flashpoint of a substance according to a first embodiment;

FIG. 3 is a timing diagram for the essential signals involved in the apparatus of the invention for measuring the flashpoint in a closed cup;

DETAILED DESCRIPTION OF THE INVENTION

Figure 2:
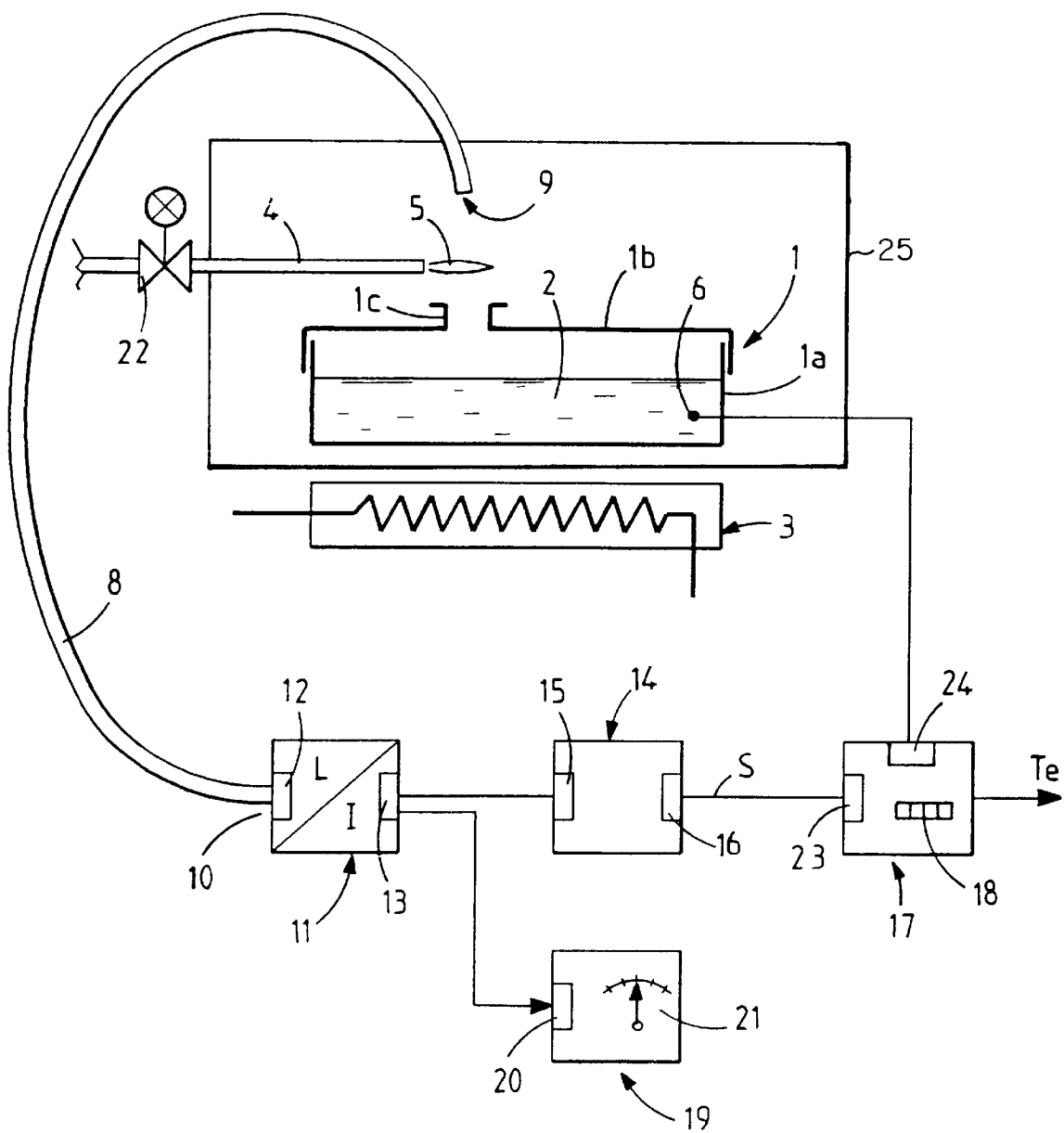
FIG. 2 shows diagrammatically a second embodiment of the invention according to which the apparatus for the closed-cup determination of the flashpoint includes an optical fiber and means for detecting flame extinction.

In general, the apparatus of the invention is used to determine the flashpoint of a flammable substance, which is defined as the lowest temperature at which the application of a flame causes ignition of the vapor emitted by the surface of the substance heated at a uniform and slow rate.

The flame is positioned in a known manner above the surface of the substance, in accordance with the standards for measuring the flashpoint, which standards are chosen depending on the nature of the substance.

FIG. 1 shows diagrammatically a first embodiment of the apparatus of the invention for automatically determining the flashpoint of a substance.

According to this first embodiment, the apparatus of the invention includes:

a test cup 1 containing the substance 2, comprising a crucible 1a and its lid 1b in the case of a closed cup and only the crucible in the case of an open cup;

means 4 and 22 for producing a flame 5;

a direct-reading thermometer 6 for measuring the temperature of the substance 2; and a detector 7 of variations in light intensity, including an indicator lamp which indicates variation in the light radiation at its input.

The detector 7 of variations in light intensity is placed so that it receives part of the light radiation emitted by the flame 5 in the case of a closed-cup determination of the flashpoint. The disappearance of the flame 5 creates a variation in light intensity at the input of the detector 7 of variations in light intensity, thereby causing the indicator lamp to be lit up.

The substance 2, heated gradually by the heating means 3, evaporates. When the vapor thus produced catches fire, the flame 5 is blown out. Since the detector 7 of variations in light intensity no longer receives light radiation, its indicator lamp lights up. At this moment, the temperature indicated by the thermometer 6 is representative of the flashpoint.

In the case of an open-cup determination of the flashpoint, the detector 7 of variations in light intensity is placed so that it receives the light radiation emitted by the vapor above the liquid 2. At the moment when the vapor catches fire, a light flash occurs at the surface of the liquid 2 which causes a variation in the light radiation received by the detector 7 of variations in light intensity, which variation causes the indicator lamp to light up. At this moment, the temperature indicated by the thermometer 6 is representative of the flashpoint.

FIG. 2 shows diagrammatically a particular embodiment of the apparatus of the invention for the closed-cup detection of the flashpoint, in which this apparatus includes:

a test cup 1 containing the substance 2, comprising a crucible 1a and its lid 1b provided with an opening 1c;

means 3 for electrically heating the substance 2;

means 4 and 22 for producing a flame 5;

an element 6 for measuring the temperature T of the substance 2;

an optical fiber 8;

a converter 11 which converts light into an electrical signal;

a module 14 for detecting the disappearance of the flame 5;

an electronic device 17; and an indicator 19 of the size of the flame 5.

The means 3 for heating the substance 2 comprise a resistance heating element and electrical supply and control means, not shown in FIG. 2. The control means provide for an adjustable temperature rise of the substance 2, for example rising by 2 to 3 degrees per minute. The flame 5 is produced at the end of a tube 4 0.8 mm in internal diameter, in which tube a combustible gas flows, the flow rate of which is adjusted by acting on the needle valve 22 so as to obtain a flame 5 approximately 4 mm in length.

The flame 5, placed just above the opening 1c of the lid 1b, illuminates the flat first end 9 of the optical fiber 8, the second end 10 of which is connected to the optical input 12 of the converter 11 which converts light into an electrical signal.

Thus, part of the light radiation emitted by the flame 5 is sensed by the flat face of the first end 9 of the optical fiber 8, then transmitted by the said optical fiber 8 through its second end 10, to the optical input 12 of the converter 11, and converted into an electrical signal which appears on the output 13 of the said converter 11. The amplitude of this electrical signal is representative of the illumination of the flat face of the first end 9 of the optical fiber 8 by the flame 5.

The output 13 of the converter 11 is linked to the input 15 of the module 14 for detecting the disappearance of the flame 5, which includes a threshold circuit. The output 16 of the module 14 for detecting the disappearance of the flame delivers a binary signal, one of the states of which is representative of the absence of flame 5. The output 16 of the module 14 for detecting the disappearance of the flame 5 is linked to the input 23 of the electronic device 17.

The element 6 for measuring the temperature T of the substance 2 is linked to the input 24 of the electronic device 17 which thus receives an electrical signal representative of the temperature T.

When the signal representative of the absence of flame 5 appears on the input 23, the device 17 records the value of the temperature T and displays it on a digital indicator 18.

Due to the effect of the increase in its temperature T, the substance 2 evaporates. The vapor thus formed ignites when the temperature T of the substance reaches the value of the flashpoint. The flame 5 disappears, blown out as a result of this ignition. The variation in illumination of the first end 9 of the optical fiber 8 which results therefrom triggers, according to the procedure described above, the recording of the temperature T which is representative of the flashpoint of the substance and its display on the indicator 18.

According to another characteristic of the apparatus of the invention, the analogue output 13 of the light converter 11 is linked to the input 20 of the indicator 19, the indication of which is proportional to the amplitude of the signal emitted by the output 13 of the converter 11, which is itself representative of the radiation emitted by the flame 5 and therefore of the size thereof.

By virtue of this indicator, precise adjustment and control of the size of the flame 5 is possible by acting on the needle valve 22.

In order to make the apparatus of the invention insensitive to ambient light radiation and to ambient disturbances, such as draughts, the test cup 1, part of the tube 4 and part of the optical fiber 8, on the side where its end 9 lies, are enclosed in an opaque enclosure 25.

By virtue of the indicator 19, adjustment of the size of the flame 5 is still possible, although it is concealed by the opaque enclosure 25.

FIG. 3 shows the variation over time of the electrical signal S applied to the input 23 of the electronic device 17 and of the value of the temperature T of the substance. The sudden variation in the signal S determines the time te at which the flame 5 is extinguished during the approximately linear temperature rise of the substance. The value of the flashpoint is equal to the temperature Te measured at the time te.

Figure 4:
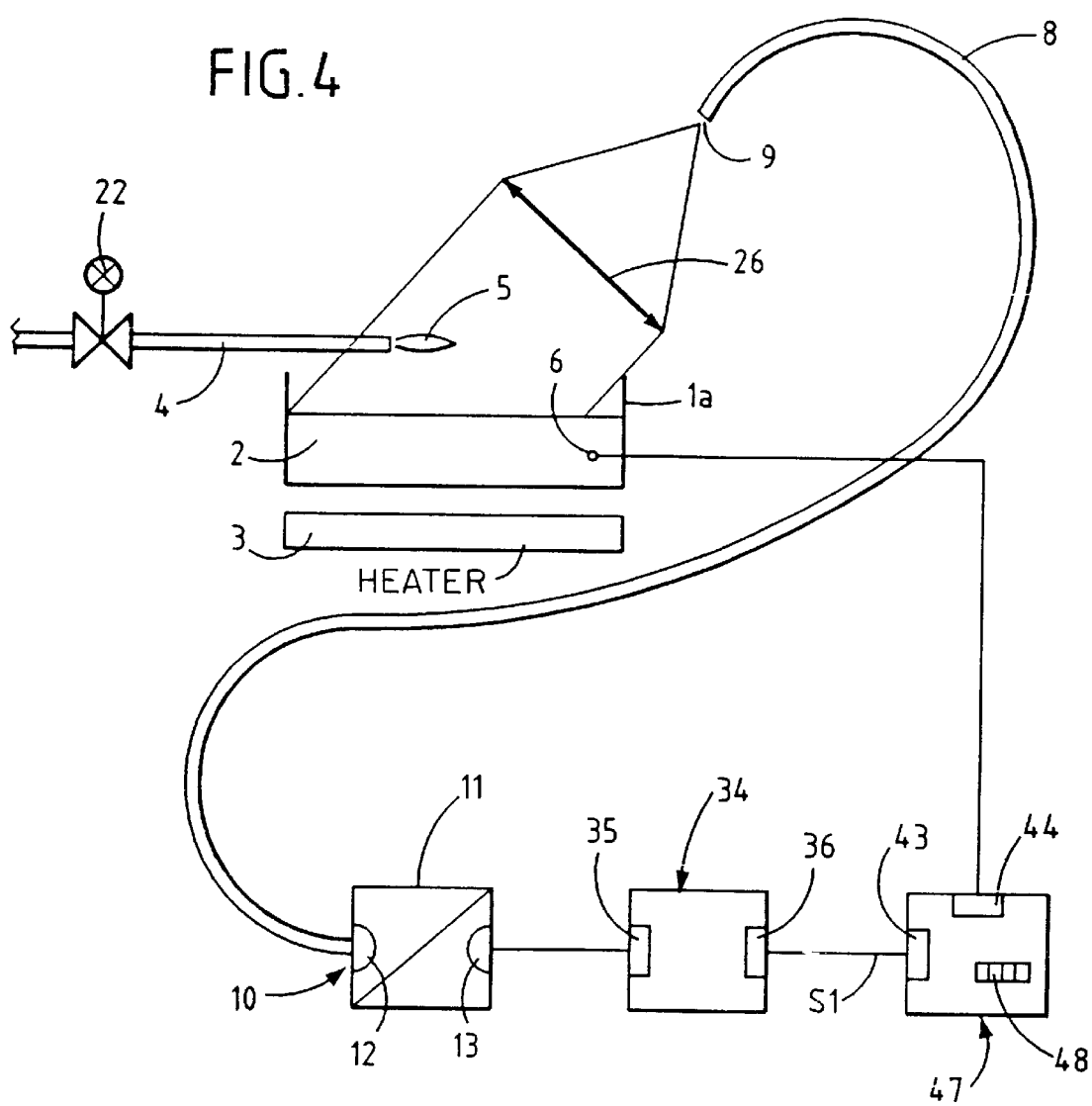
FIG. 4 shows diagrammatically a third embodiment of the invention for the open cup determination of the flashpoint, according to which the apparatus includes a lens and an optical fiber.

FIG. 4 shows diagrammatically an embodiment of the apparatus of the invention for the open-cup detection of the flashpoint, according to which it includes:

a test cup 1 containing the substance 2, consisting of the crucible 1a;

means 3 for electrically heating the substance 2;

means 4 and 22 for producing a flame 5;

an element 6 for measuring the temperature T of the substance 2;

an optical converging lens 26;

an optical fiber 8;

a converter 11 which converts light into an electrical signal;

a light-flash detection module 34; and an electronic device 47.

The means 3 for heating the substance 2 comprise a resistance heating element and electrical supply and control means, not shown in FIG. 4. The control means provide for an adjustable temperature rise of the substance 2, for example rising by 2 to 3 degrees per minute. The flame 5 is produced at the end of a tube 4 which is 0.8 mm in internal diameter, in which tube a combustible gas flows, the flow rate of which is adjusted by acting on the needle valve 22 so as to obtain a flame 5 which is 4 mm in length.

The flame 5 is positioned just above the surface of the liquid 2.

The lens 26 is placed above the liquid 2, its axis of symmetry making an angle, for example 45 degrees, with respect to the surface of the liquid in order to reduce the possibility of dust being deposited on its faces.

The flat first end 9 of the optical fiber 8 is placed approximately at the optical focus of the lens 26, the second end 10 of the optical fiber being connected to the optical input 12 of the converter 11 which converts light into an electrical signal.

Thus, part of the light radiation emitted by the vapor above the surface of the liquid 2 is sensed by the flat face of the first end 9 of the optical fiber 8, then transmitted by the said optical fiber 8 through its second end 10, to the optical input 12 of the converter 11, and is converted into an electrical signal which appears on the output 13 of the said converter 11. The amplitude of this electrical signal is representative of the illumination of the flat face of the first end 9 of the optical fiber 8 by the flame 5 and the surface of the liquid 2.

The output 13 of the converter 11 is linked to the input 35 of the light-flash detection module 34 which includes a voltage-peak detection circuit. The output 36 of the light-flash detection module 34 delivers a binary signal, one of the states of which is representative of the appearance of a light peak on the flat face of the first end 9 of the optical fiber 8. The output 36 of the light-flash detection module 34 is linked to the input 43 of the electronic device 47.

The element 6 for measuring the temperature T of the substance 2 is linked to the input 44 of the electronic device 47 which thus receives an electrical signal representative of the temperature T.

When the vapor emitted by the heated substance 2 ignites, a light flash is produced at the surface of the said substance, which flash illuminates the flat face of the first end 9 of the optical fiber 8. This flash is transmitted via the optical fiber 8 to the input 12 of the converter 11 which produces an electrical signal representative of the light intensity of the illumination on its output 13. The module 34 receives this signal on its input 35 and generates, on its output 36, a binary signal which is applied to the input 43 of the device 47. The device 47 records the value of the temperature Te of the substance 2 at this time te and displays it on a digital indicator 48. This value Te is representative of the value of the open-cup flashpoint of the substance 2.

Figure 6:
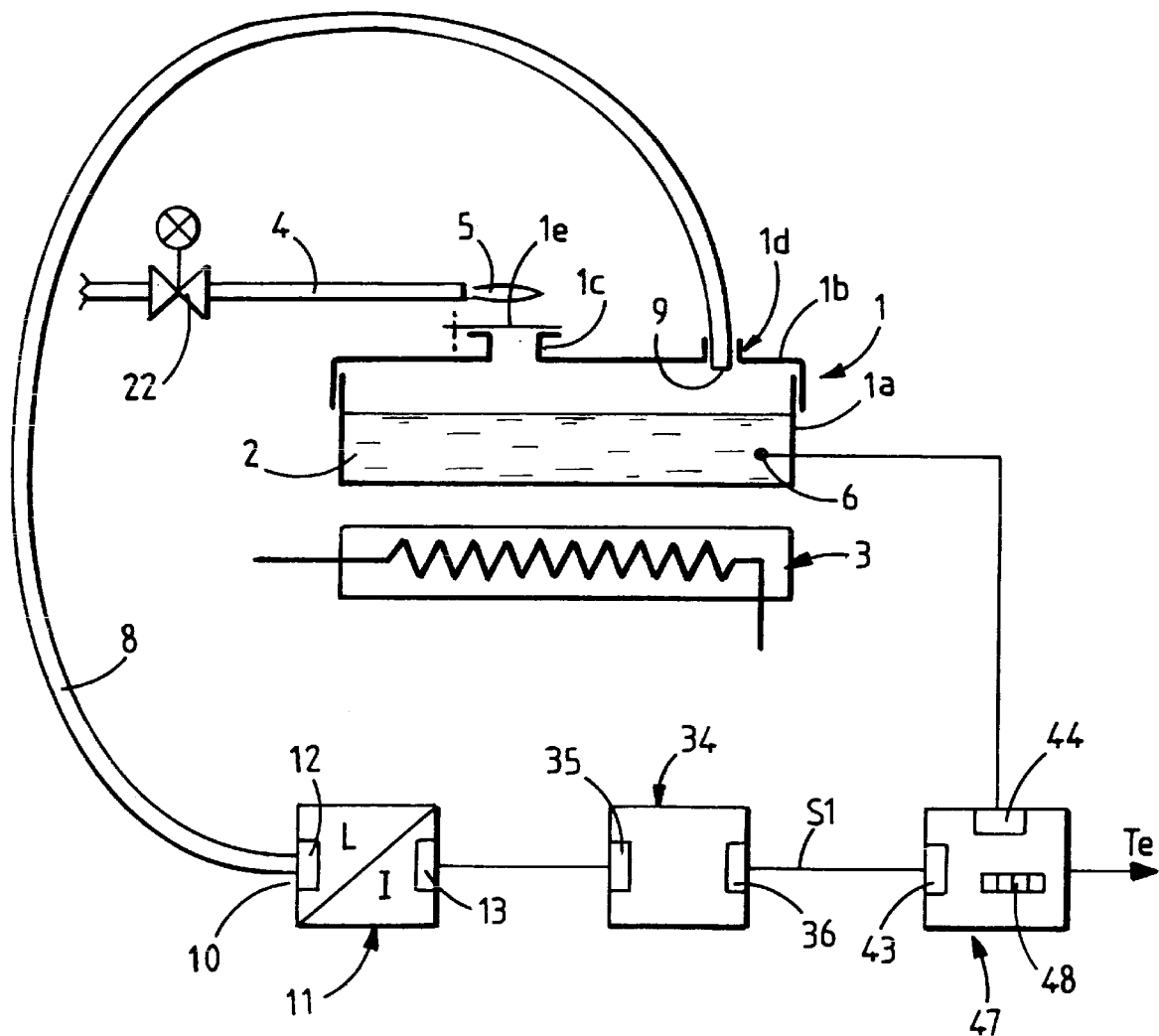
FIG. 6 shows diagrammatically a fourth embodiment of the invention for the closed cup determination of the flashpoint, in a according to which the apparatus of the invention includes a fiber and means for detecting the appearance of a light flash.

FIG. 6 shows diagrammatically a particular embodiment of the apparatus of the invention for the closed-cup detection of the flashpoint, in which this apparatus includes:

- a test cup 1 containing the substance 2, comprising a crucible 1a and its lid 1b provided with two openings 1c and 1d and with a controllable closure shutter 1e;
- means 3 for electrically heating the substance 2;
- means 4 and 22 for producing a flame 5;
- an element 6 for measuring the temperature T of the substance 2;
- an optical fiber 8;
- a converter 11 which converts light into an electrical signal;
- a light-flash detection module 34; and
- an electronic device 47.

The means 3 for heating the substance 2 comprise a resistance heating element and electrical supply and control means, not shown in FIG. 2. The control means provide for an adjustable temperature rise of the substance 2, for example rising by 2 to 3 degrees per minute. The flame 5 is produced at the end of a tube 4 which is 0.8 mm in internal diameter, in which tube a combustible gas flows, the flow rate of which is adjusted by acting on the needle valve 22 so as to obtain a flame 5 approximately 4 mm in length.

The flame 5 is placed just above the shutter 1e closing off the opening 1c of the lid 1b. The first end 9 of the optical fiber is placed inside the cup above the substance 2, the optical fiber 8 entering the cup 1 through the opening 1d of the lid 1b.

Thus, the flat face of the first end 9 of the optical fiber 8 senses part of the light radiation emitted by the vapor emitted by the heated substance 2, and transmits it via the said optical fiber 8 through to its second end 10, to the optical input 12 of the converter 11. This converter 11 converts the light radiation received on its input 12 into an electrical signal which appears on its output 13. The amplitude of this electrical signal is representative of the illumination of the flat face of the first end 9 of the optical fiber 8.

The output 13 of the converter 11 is linked to the input 35 of the light-flash detection module 34 which includes a circuit for detecting an electrical signal peak. The output 36 of the light-flash detection module 34 delivers a binary electrical signal, one of the states of which is representative of the appearance of a light peak on the flat face of the first end 9 of the optical fiber 8. The output 36 of the light-flash detection module 34 is linked to the input 43 of the electronic device 47.

The element 6 for measuring the temperature T of the substance 2 is linked to the input 44 of the electronic device 47 which thus receives an electrical signal representative of the temperature T.

At regular temperature intervals of the substance 2, the closure shutter 1e is moved so as to expose the opening 1c via which the flame 5 is directed into the cup 1. After presentation of the flame 5 above the liquid 2, it is removed and the closure shutter closed again.

When the vapor emitted by the heated substance 2 ignites, a light flash is produced at the surface of the said substance, which flash illuminates the flat face of the first end 9 of the optical fiber 8. This flash is transmitted via the optical fiber 8 to the input 12 of the converter 11 which produces an electrical signal representative of the light intensity of the illumination on its output 13. The module 34 receives this signal on its input 35 and generates, on its output 36, a binary signal which is applied to the input 43 of the device 47. The device 47 records the value of the temperature Te of the substance at this time te and displays it on a digital indicator 48. This value Te is representative of the value of the open-cup flashpoint of the substance 2.

Figure 5:
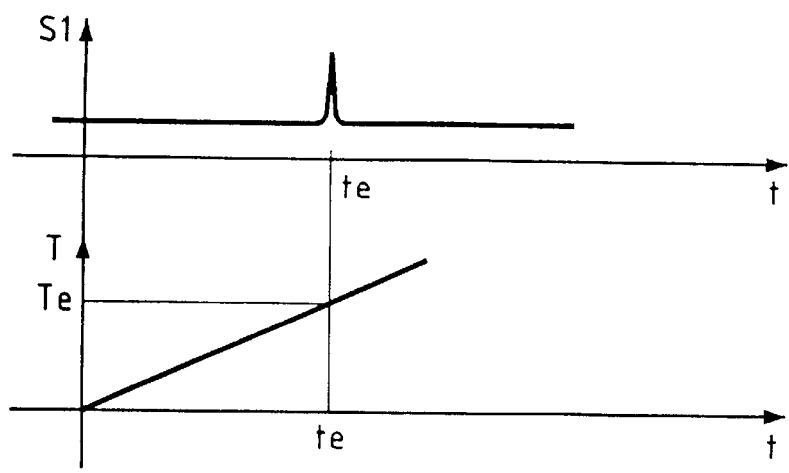
FIG. 5 is a timing diagram for the essential signals involved in the apparatus of the invention for measuring the flashpoint in an open cup.

FIG. 5 shows the variation over time in the electrical signal S1 applied to the input 43 of the electronic device 47 and in the value of the temperature T of the substance. The peak in the variation in the signal S1 determines the time te at which the vapor of the heated liquid 2 ignites. The value of the flashpoint is equal to the temperature Te measured at the time te.

Figure 7:
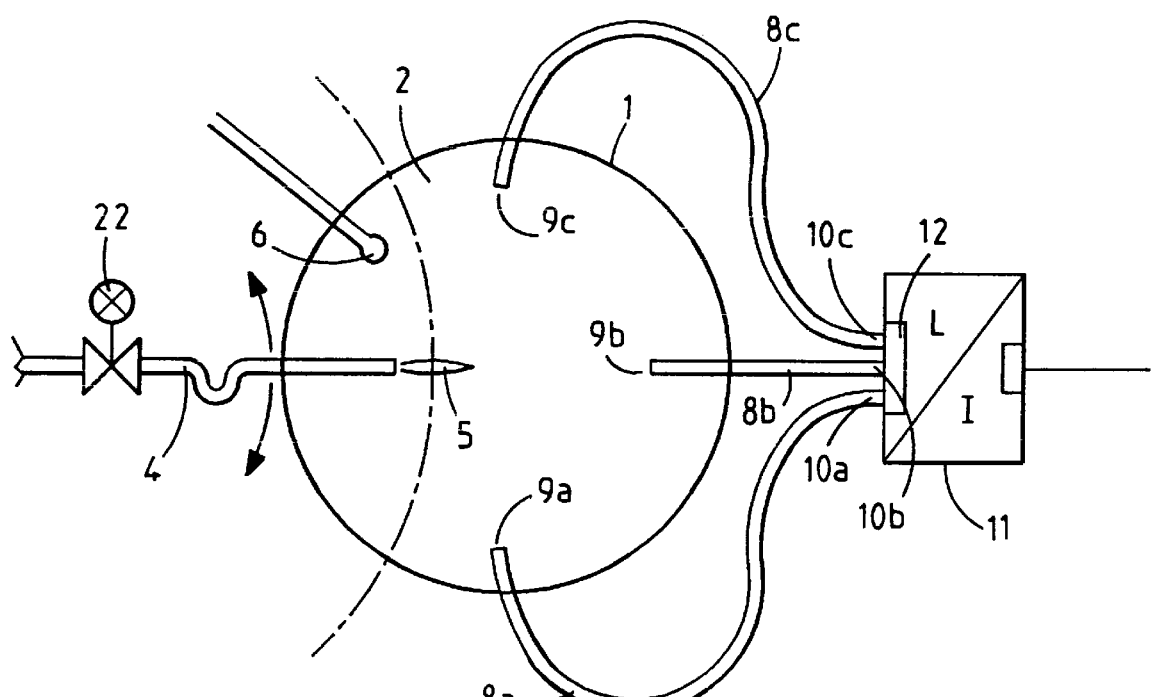
FIG. 7 shows diagrammatically a fifth embodiment of the invention for the open cup determination of the flashpoint, in an according to which the apparatus includes three optical fibers.

A variant of the third embodiment is shown in FIG. 7, according to which variant the apparatus of the invention includes a movable tube 4 for producing the flame 5, which is moved to the surface of the liquid 2, and three optical fibers 8a, 8b and 8c. These three fibers sense part of the light radiation emitted by the illumination which results from the ignition of the vapor of the substance 2, on their first ends 9a, 9b and 9c. The second ends 10a, 10b and 10c of the fibers 8a, 8b and 8c are linked to the input 12 of the converter 11 which converts light into an electrical signal.

The embodiments described above are given by way of non-limiting examples, the means of the invention being able to be easily adapted to other types of apparatuses for the open-cup or closed-cup determination of the flashpoint.

We claim:

1. Apparatus for determining the flashpoint of a substance, comprising;
   - a test cup adapted to contain the substance,
   - a heating element configured to heat the substance,
   - a flame calibrator configured to produce a calibrated flame,
   - a temperature sensor configured to measure the temperature of the substance, and
   - an optical detector configured to detect variations in light intensity,
   - wherein the optical detector includes at least one optical fiber having a first end.

2. Apparatus according to claim 1, further comprising;
   - a lid closing the test cup and having an opening for presentation of the flame,
   - wherein the first end of the optical fiber is placed outside the test cup so as to sense part of a light radiation emitted by the flame, and
   - said part of the light radiation propagates inside the optical fiber as far as the second end.

3. Apparatus according to claim 2, further comprsing:
   - a light converter which converts light into a first electrical signal, said light converter having an optical input to which the second end of the optical fiber is connected, and an electrical analogue output;
   - a module which detects the disappearance of the flame, provided with an analogue input linked to the analogue output of the light converter and with a logic output which delivers a second electrical signal indicative of the disappearance of the flame; and
   - an electronic device connected to the logic output of the module which detects the disappearance of the flame and to the temperature sensor, said electronic device configured to record the value of the temperature of the substance at the moment when the second electrical signals indicative of the disappearance of the flames, appears.

4. Apparatus according to claim 3 further comprising an indicator configured to indicate the size of the flame, provided with an input connected to the electrical analogue output of the light converter.

5. Apparatus according to claim 2 or 3, further comprising an opaque enclosure configured to enclose the test cup, the the flame calibrator and the first end of the optical fiber.

6. Apparatus according to claim 5, further comprising an indicator configured to indicate the size of the flame, and provided with an input connected to the electrical analogue output of the light converter.

7. Apparatus according to claim 1, wherein:
the optical detector includes a converging lens placed above the surface of the substance,
the first end of the optical fiber is placed at an optical focus of the converging lens so as to sense part of a light radiation emitted by a vapor of the substance, said vapor being ignited by the flame, and
said part of the light radiation propagates inside the optical fiber as far as the second end.

8. Apparatus according to claim 1, further comprising:
a lid closing the test cup and having a first opening for presentation of the flame to a vapor of the substance, a second opening for placing the first end of the optical fiber inside the test cup so as to sense part of a light radiation emitted by the vapor of the substance,
wherein said vapor is ignited by the flame, and said part of the light radiation propagates inside the optical fiber as far as the second end.

9. Apparatus according to claim 7 or 8, further comprising:
a light converter which converts light into a first electrical signal, said light converter having an optical input, to which the second end of the optical fiber is connected, and an electrical analogue output;
a light-flash detection module provided with an analogue input linked to the analogue output of the light converter and with a logic output which delivers a second electrical indicative of the ignition of the vapor of the substance; and
an electronic device connected to the logic output of the light-flash detection module and to the temperature sensor, said electronic device configured to record the temperature of the substance at a moment when the vapor of the substance is ignited by the flame.

* * * * *